United States Patent
Kodra et al.

(10) Patent No.: US 9,959,549 B2
(45) Date of Patent: May 1, 2018

(54) MENTAL STATE ANALYSIS FOR NORM GENERATION

(71) Applicant: Affectiva, Inc., Waltham, MA (US)

(72) Inventors: Evan Kodra, Waltham, MA (US); Rana el Kaliouby, Milton, MA (US); Timothy Peacock, Concord, MA (US); Gregory Poulin, Acton, MA (US)

(73) Assignee: Affectiva, Inc., Boston, MA (US)

( * ) Notice: Subject to any disclaimer, the term of this patent is extended or adjusted under 35 U.S.C. 154(b) by 25 days.

(21) Appl. No.: 14/598,067

(22) Filed: Jan. 15, 2015

(65) Prior Publication Data

US 2015/0142553 A1 May 21, 2015

Related U.S. Application Data

(63) Continuation-in-part of application No. 13/153,745, filed on Jun. 6, 2011.

(Continued)

(51) Int. Cl.
*G06K 9/00* (2006.01)
*G06Q 30/02* (2012.01)
(Continued)

(52) U.S. Cl.
CPC ......... *G06Q 30/0242* (2013.01); *A61B 5/165* (2013.01); *G06F 19/3406* (2013.01);
(Continued)

(58) Field of Classification Search
CPC ........... G06K 9/00275; G06K 9/00281; G06K 9/0028; G06K 9/00295; G06K 9/00302;
(Continued)

(56) References Cited

U.S. PATENT DOCUMENTS 3,034,500 A 5/1962 Backster, Jr.
3,548,806 A 12/1970 Fisher
(Continued)

FOREIGN PATENT DOCUMENTS

JP 08115367 7/1996
KR 10-2005-0021759 A 3/2005
(Continued)

OTHER PUBLICATIONS

Rana Ayman El Kaliouby, Mind-reading machines: automated inference of complex mental states, Jul. 2005, University of Cambridge, Cambridge, United Kingdom.
(Continued)

*Primary Examiner* — Wesley Tucker
(74) *Attorney, Agent, or Firm* — Adams Intellex, PLC

(57) ABSTRACT

Mental state data is gathered from a plurality of people and analyzed in order to determine mental state information. Metrics are generated based on the mental state information gathered as the people view media presentations. Norms, defined as the quantitative measures of the mental states of a plurality of people as they view the media presentation, are determined based on the mental state information metrics. The norms can be determined based on various viewer criteria including country of residence, demographic group, or device type on which the media presentation is viewed. Responses to new media are then compared against norms to determine the effectiveness of the new media presentations.

25 Claims, 10 Drawing Sheets

Related U.S. Application Data

(60) Provisional application No. 61/927,481, filed on Jan. 15, 2014, provisional application No. 61/953,878, filed on Mar. 16, 2014, provisional application No. 61/972,314, filed on Mar. 30, 2014, provisional application No. 62/023,800, filed on Jul. 11, 2014, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011.

(51) Int. Cl.
 *G06F 19/00* (2018.01)
 *A61B 5/16* (2006.01)
 *A61B 5/00* (2006.01)

(52) U.S. Cl.
 CPC ...... *G06F 19/3418* (2013.01); *G06F 19/3431* (2013.01); *G06F 19/3481* (2013.01); *G06Q 30/0271* (2013.01); *A61B 5/0077* (2013.01)

(58) Field of Classification Search
 CPC ........... G06K 9/00308; G06K 9/00315; G06K 9/00335; G06K 9/00342; G06K 9/00348; G06K 9/00355; G06K 9/00362; G06K 9/00241
 See application file for complete search history.

(56) References Cited

U.S. PATENT DOCUMENTS

| | | |
|---|---|---|
| 3,870,034 A | 3/1975 | James |
| 4,353,375 A | 10/1982 | Colburn et al. |
| 4,448,203 A | 5/1984 | Williamson et al. |
| 4,794,533 A | 12/1988 | Cohen |
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstrom et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ball et al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 * | 4/2011 | Sharma ............ G06Q 20/3674 705/14.49 |
| 8,010,458 B2 | 8/2011 | Galbreath et al. |
| 8,401,248 B1 | 3/2013 | Moon et al. |
| 8,442,638 B2 | 5/2013 | Libbus et al. |
| 8,522,779 B2 | 9/2013 | Lee et al. |
| 8,529,447 B2 | 9/2013 | Jain et al. |
| 8,540,629 B2 | 9/2013 | Jain et al. |
| 8,600,120 B2 | 12/2013 | Gonion et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |

(56) References Cited

U.S. PATENT DOCUMENTS

| | | |
|---|---|---|
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0078513 A1 | 4/2003 | Marshall |
| 2003/0093784 A1 | 5/2003 | Dimitrova et al. |
| 2003/0191682 A1 | 10/2003 | Shepard et al. |
| 2003/0191816 A1 | 10/2003 | Landress et al. |
| 2004/0181457 A1 | 9/2004 | Biebesheimer et al. |
| 2005/0187437 A1 | 8/2005 | Matsugu et al. |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0115157 A1 | 6/2006 | Mori |
| 2006/0143647 A1 | 6/2006 | Bill |
| 2006/0235753 A1 | 10/2006 | Kameyama |
| 2007/0167689 A1 | 7/2007 | Ramadas et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1 | 11/2008 | Kurtz et al. |
| 2009/0002178 A1 | 1/2009 | Guday et al. |
| 2009/0006206 A1 | 1/2009 | Groe et al. |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0210290 A1 | 8/2009 | Elliott et al. |
| 2009/0217315 A1 | 8/2009 | Malik et al. |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2011/0092780 A1 | 4/2011 | Zhang et al. |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0196855 A1 | 8/2011 | Wable et al. |
| 2011/0231240 A1 | 9/2011 | Schoen et al. |
| 2011/0251493 A1 | 10/2011 | Poh et al. |
| 2011/0263946 A1 | 10/2011 | el Kaliouby et al. |
| 2012/0293548 A1 | 11/2012 | Perez et al. |
| 2012/0302904 A1 | 11/2012 | Lian et al. |
| 2012/0304206 A1 | 11/2012 | Roberts et al. |
| 2013/0006124 A1 | 1/2013 | Eyal et al. |
| 2013/0023337 A1 | 1/2013 | Bowers et al. |
| 2013/0116587 A1 | 5/2013 | Sornmo et al. |
| 2013/0197409 A1 | 8/2013 | Baxter et al. |
| 2016/0055236 A1* | 2/2016 | Frank ............... G06Q 30/02 707/748 |
| 2016/0300252 A1* | 10/2016 | Frank ............ G06Q 30/0203 |

FOREIGN PATENT DOCUMENTS

| | | |
|---|---|---|
| KR | 10-2008-0016303 A | 2/2008 |
| KR | 1020100048688 A | 5/2010 |
| KR | 100964325 B1 | 6/2010 |
| KR | 1020100094897 A | 8/2010 |
| WO | WO 2011/045422 A1 | 4/2011 |

OTHER PUBLICATIONS

International Search Report dated Nov. 14, 2011 for PCT/US2011/39282.

International Search Report dated Apr. 16, 2012 for PCT/US2011/054125.

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG-EBGM." Pattern Recognition Letters 29.10 (2008): 1537-1541.

* cited by examiner

MENTAL STATE ANALYSIS FOR NORM GENERATION

RELATED APPLICATIONS

This application claims the benefit of U.S. provisional patent applications "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014. This application is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011. The foregoing applications are each hereby incorporated by reference in their entirety.

FIELD OF ART

This application relates generally to analysis of mental states and more particularly to generating and using norms in mental state analysis.

BACKGROUND

On any given day, an individual is confronted with a dizzying array of external stimuli. The stimuli can be any combination of visual, aural, tactile, and other types of stimuli, and, alone or in combination, can invoke strong emotions in a given individual. An individual's reactions to received stimuli are important components that define the essence of the individual. Further, the individual's responses to the stimuli can have a profound impact on the mental states experienced by the individual. The mental states of an individual can vary widely, ranging from happiness to sadness, from contentedness to worry, and from calm to excitement, to name a few possible states. Some familiar examples of mental states or emotional states that are often experienced as a result of common stimuli include frustration or disgust during a traffic jam, disappointment from arriving at a shop just after closing time, boredom while standing in line, distractedness while listening to a crying child, delight while viewing a cute puppy video, and impatience while waiting for a cup of coffee. People's mental states influence how they interact with others. Individuals may become perceptive of and empathetic towards those around them based on evaluating and understanding the mental states of the same people. While an empathetic person can easily perceive another person's anxiety or joy and respond accordingly, automated understanding or quantifying of mental states is a far more challenging undertaking. The ability and techniques by which one person perceives another's mental state or states can be quite difficult to summarize or relate to others. In fact when asked to recount how this perception occurs, people often respond by claiming the perceptive feelings originate from a visceral response or "gut feel."

Many mental states of an individual or group of individuals can be identified and quantified to aid in the understanding of the behavior of the individual or the group of individuals. As one example, individuals who are able to understand their emotional state can choose to use the known mental state information in a variety of practical ways. Similarly, other individuals and observers can use known mental state information about themselves or those around them for the individuals' or observers' own benefit or for the benefits of others. A familiar example is seen in the example of people collectively responding with fear or anxiety after witnessing a catastrophe. Likewise, people can collectively respond with happy enthusiasm when a sports team that they support wins a major victory.

SUMMARY

The mental states of a plurality of people are analyzed to generate norms as the people view media presentations on any of a variety of devices. The norms provide quantitative measurements relating to the mental states of the viewers as they view the media presentations. One or more devices are used to gather mental state data from the plurality of people. The mental state data is analyzed to produce mental state information. One or more metrics are then generated using the mental state information. One or more norms are evaluated based on the one or more metrics. A norm for a class or type of media presentation is compared against an advertisement or another media presentation to determine the responses of the viewer or viewers of the media presentation. A computer-implemented method for mental state analysis is disclosed comprising: obtaining mental state data from a plurality of people; analyzing the mental state data to produce mental state information for the plurality of people; generating a metric based on the mental state information; and evaluating a norm based on the metric. A norm can be determined for a device type. A norm can be determined for a product category. A norm can be determined for a certain demographic.

In embodiments, a computer system for mental state analysis comprises: a memory which stores instructions; one or more processors attached to the memory wherein the one or more processors, when executing the instructions which are stored, are configured to: obtain mental state data from a plurality of people; analyze the mental state data to produce mental state information for the plurality of people; generate a metric based on the mental state information; and evaluate a norm based on the metric. In some embodiments, a computer-implemented method for physiology analysis comprises: receiving mental state data from a plurality of people; analyzing the mental state data to produce mental state information for the plurality of people; generating a metric based on the mental state information; and evaluating a norm based on the metric. In embodiments, a computer-implemented method for mental state analysis comprises: receiving mental state information based on analysis of mental state data obtained from a plurality of people along with a metric based on the mental state information and a norm based on the metric; and rendering an output of the norm.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
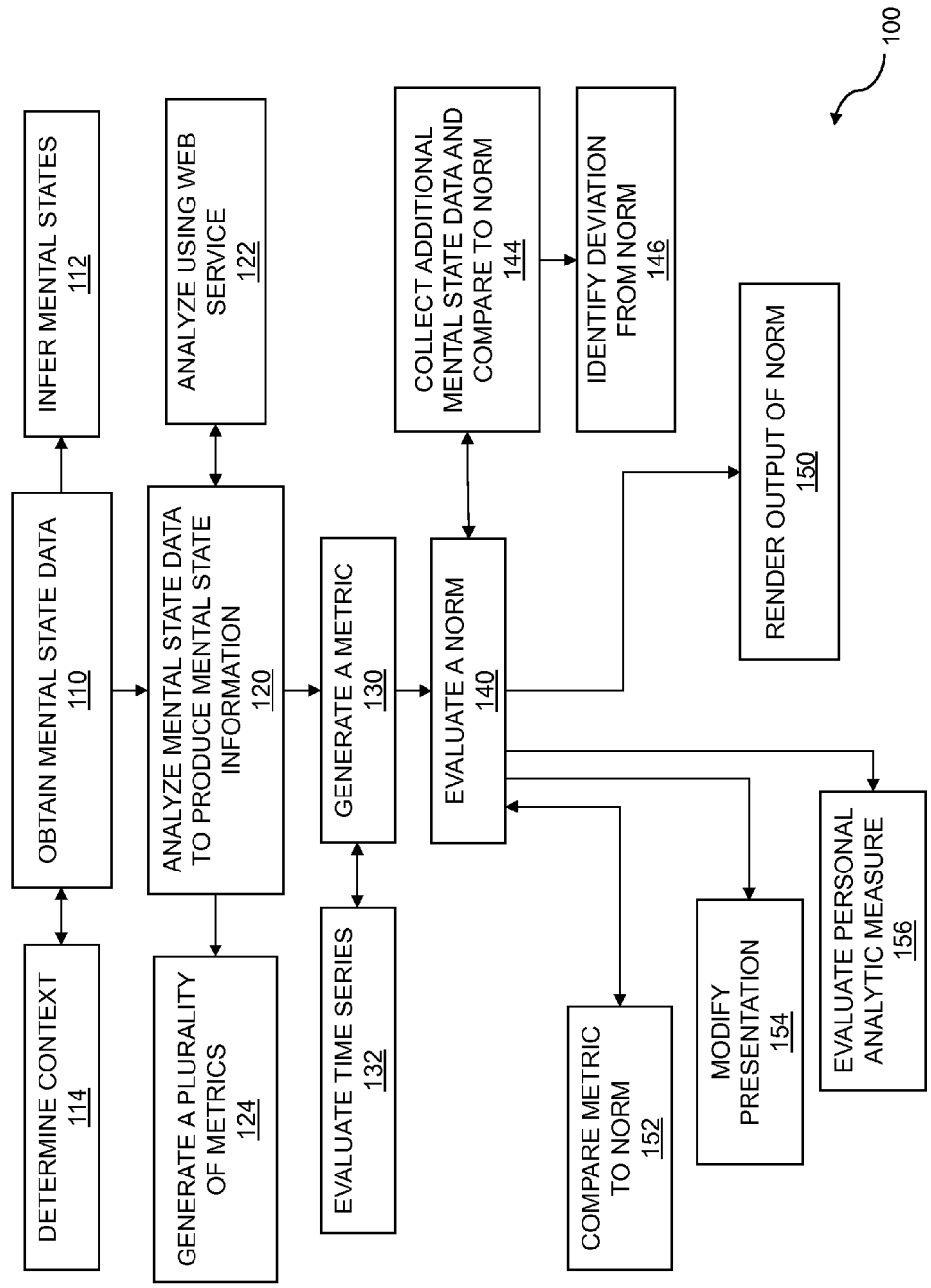
FIG. 1 is a flow diagram for norms and mental state analysis.

People experience mental states as they view and interact with the world around them. Mental states can manifest as people view movies, videos, television, advertisements, and various other forms of media presentations. Understanding the ways in which mental states occur as part of normal responses to various media, as well as times and situations which exhibit deviations from these norms, can provide profound insight into the media as well as being able to determine ways to optimize the media. Numerous types of media presentations can be evaluated, with advertisements representing one example media presentation type of significant interest. Various media presentations can be selected and improved in order to enhance the media presentations, make the presentations more likely to go viral, make them more memorable, make them more likeable, and so on.

In embodiments of the mental-state aided media evaluation process, mental states are analyzed and norms are determined for the mental states. Norms provide a quantifiable measure of the mental states of people as they view media presentations, a way to understand and classify a collective group mental response. In embodiments, the generation of norms is based on metrics, which are in turn created from mental state information collected from multiple people. The norms can be useful in the comparison of more recently presented media presentations to typical collective responses to similar previous presentations. Mental state data can include images captured by one or more cameras attached to a device used by an individual, cameras attached to other devices, webcams, adjacent cameras, and so on. The metrics can be evaluated to produce a norm derived from the metrics of a group of people. The norms can be used for analysis of a variety of sub-groups or people, media presentations, and devices on which the media presentations are communicated. The norms can provide for a numerical value for comparison purposes.

Mental states are analyzed in light of media presentations that are viewed. When a new media presentation, such as a new advertisement, is analyzed and metrics for the mental states are evaluated, the newly-derived metrics can be compared with norms for similar types of advertisements. Deviations from the norms are used to evaluate new media presentations, with a new media presentation being significantly different from a mental state norm able to serve as an indicator of a new presentation's performance against a baseline, depending on the implemented mental state metric and the observed reaction. For example, a higher than normal valence metric can indicate that the new media presentation is highly effective in attracting and maintaining audience attention and provoking positive emotional responses. As valence can be considered a measure of the emotional positivity provoked by a stimuli, an advertisement that is well above the corresponding norm for valence has a high probability of becoming a viral hit. In order to further refine and interpret deviations, norms can be established for various demographic groups, for various types of media presentations, and even for various types of devices on which the media presentation is observed.

FIG. 1 is a flow diagram for norms and mental state analysis. A flow 100 that describes a computer-implemented method for mental state analysis for norm generation is shown. The flow 100 includes obtaining mental state data 110 from a plurality of people. The mental state data is obtained through a variety of techniques including image capture of one or more individuals. Cameras or other imaging devices can capture the image data. The cameras or imaging devices can be included in a device being used by the plurality of people or can be positioned with a view of the plurality of people. The mental state data can be obtained through other techniques including collection of physiological data for the one or more individuals, recording gaze direction, and so on. The mental state data from the plurality of people can be collected while the plurality of people are exposed to a media presentation. The media presentation can include video, video clips, still images, multimedia presentations, mashups, and so on. In many embodiments, the media presentation includes an advertisement. The media presentation can include a variety of advertisements, different versions of the same advertisement, or the like. Additionally the media presentation can include other types of presentations including political campaigns, infomercials, entertainment programs, and so on. The mental state data can be collected sporadically or continuously, depending on the embodiment. The mental state data can be collected while the one or more individuals are viewing the media presentation, while the individuals are operating a device used to view the media presentation, or in any other appropriate situation. The flow 100 can further comprise inferring mental states 112 based on the mental state data which was obtained from the one or more individuals viewing the media presentation. The inferred mental states can include one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, and so on. It should be understood that throughout this disclosure, the term "mental states" can refer to emotions, emotional states, emotion states, and the like. The flow 100 can further comprise determining the context 114 during which the mental state data was captured. The determined context, or contextual information, can include details such as whether the media presentation was viewed alone or with other viewers, the location of the viewing, the device on which the media presentation was viewed, and so on.

The flow 100 includes analyzing the mental state data to produce mental state information 120. The mental state data collected from the one or more individuals can be analyzed to determine the mental state information pertaining to the individuals. Various techniques can be used to perform the analysis, which can be based on algorithms, heuristics, general-purpose analysis programs, and so on. The mental state information can be used to determine smiles, frowns, eyebrow raises, and other facial expressions; projected sales of goods or services; expressiveness; the wellbeing of the viewer; and so on. The device which is being used for the media presentation can perform the data analysis or some or all of the analyzing of the mental state data can be performed by a web service 122. The web service can comprise one or more remote servers, a cloud-based service or server, and so on. The flow 100 can further include generating a plurality of metrics 124 based on the mental state information. The metrics can be based on various types of analysis of the mental state information. The metrics can include probabilities, means, variabilities, and other statistical values or any other appropriate values derived from the mental state information. The metrics can be based on one or more mental states and can include valence, smile, expressiveness, dislike, concentration, and so on.

The flow 100 includes generating a metric 130 based on the mental state information. As has been discussed previously, the metric can be used to apply a numeric value to mental state information resulting from analysis of the mental state data obtained from one or more people as they view a media presentation. The metric can include a mean value and a variability value determined for one or more mental states. The mean and variability values can include values representing stress, sadness, happiness, anger, attention, surprise, concentration, dislike, expressiveness, smile, valence, and so on. The metric can be calculated for one or more media presentations where the media presentations can include thumbnails of advertisements. The metric can be used to compare advertisements. The metric can be calculated by evaluating a time series 132 of the mental state information. The metric can be based on a continuous time series, a segment of a time series, and so on. Further, the norm can include a mean value and a standard deviation value indicative of a mental state and variability on the mental state where the norm indicates a collective response by the plurality of people to a media presentation. The collective response can provide insight on how a group of people perceive the media presentation and what their emotional reactions are.

The flow includes evaluating a norm 140 based on the metric. A norm is a quantitative measure of a mental state, a representation of a mental state, and so on. A norm can be based on a statistical value, for example an expected value, or another value associated with a metric. The norm can be based on a combination of a plurality of metrics. The norm can be determined for a certain demographic. The norm can be determined based on two or more demographics in combination. The norm can be determined for a country, a region, a socioeconomic group, a race, an ethnicity, a language group, a market, an age group, or a gender. For example, a norm can be evaluated for a single demographic, such as women aged 25-32, or can be evaluated for a combination of demographics, such as high-earning Japanese women aged 25-32, for example. The norm can be determined for a product category such as media presentations including advertisements for fast-moving consumer goods or for financial services. The norm can also be determined for media length as well as media type with embodiments generating different norms if a presentation is in its finished form, in an animatic stage, or represented by a storyboard. Likewise, a norm can be determined for a gaze direction where the portion of a media presentation that is the focus of an individual's attention is identified. The norm can be determined for presentation type, for example, different norms can be identified for an advertisement depending on its placement in other media—pre-roll, mid-roll, or post roll. The norm can be determined for a media presentation with a specific emotional tone. One or more emotional tones can be included in the media presentation and can be used to refine and differentiate norm generation. The emotional tone can include being funny, being sentimental, being educational, motivating to action, or various other tones. The norm can be determined on a device basis. The value determined for a norm can vary based on the particular device or devices used for the viewing of a media presentation, with embodiments generating different norms for mobile devices, tablets, cell phones, or laptops. Different unique norms can also be determined for criteria such as user gaze direction and concentration. For example, gaze-direction specific norms can be generated based on a determination of which portion of a presentation a viewer's eyes are fixed on, and concentration-specific norms can be generated based on the device on which a user views a presentation, with embodiments providing a higher norm for concentration when using a laptop than when using a smartphone because a person can tend to use the laptop for work activities and the smartphone for leisure activities.

The norm can represent an emotion norm for a group of people. The emotion norm for a group can vary contingent on the group's composition. The group may be based on country, demographic, gender, and so on. For example, the value of a norm for a media presentation with a funny tone can be higher in one country than in another based on local customs, social mores, etc. The norm can be determined in response to the media presentation. The norm can be determined for a category of media presentations. The norm can be calculated across a number of media presentations.

In embodiments, the mental state data which is obtained 110 includes facial data, and the metric and the norm can be a reflection of the facial data. The facial data can include data on smiles, surprise, concentration, attention and so on. The facial data can include action units. The action units can include one or more of valence, action unit 4, action unit 12, and so on. The action units can include eyebrow raise, eyebrow lower, frown, and so on.

The flow 100 can further comprise collecting additional mental state data and comparing the additional mental state data to the norm 144. Additional mental state data can be collected based on an additional group of viewers. The group of viewers can include viewers from a different country, from different demographic groups, and so on. The additional mental state data collected can be analyzed to generate values for metrics of interest. Norms can be evaluated based on the new metric values and compared to the previously evaluated norms. Further, the flow 100 can further comprise identifying a deviation by the additional mental state data from the norm 146. The deviation by the additional mental state data from the norm can be due to collecting data from viewers in a different country, from a different demographic, and so on. A deviation from the norm can indicate different cultural preferences or other differences between the groups of users from whom the datasets have been collected. The deviation from the norm can be used in the generation of an emotional profile. The emotional profile can indicate a viewer's or group of viewers' distinctive features or characteristics. The emotional profile can include information on distinctive habits, attitudes, qualities, behaviors, and emotional traits of an individual or group of individuals. The deviation can be used to select a media presentation. For example, a media presentation with the most favorable response from a group of viewers can be chosen for display to the same group of viewers or to another group of viewers with similar characteristics. The selection of the media presentation can be automatic. The deviation can be determined when the additional mental state data falls outside the confidence interval. A confidence interval can be determined for metrics and norms of interest. When the additional mental state data falls outside any of the determined confidence intervals, then confidence that a deviation is present can be high.

The flow 100 can further comprise rendering an output 150 of the norm. An output of a norm can be rendered in order to display the norm. The rendering can be on an electronic display, where the electronic display can include a handheld device such as a smartphone or PDA, a portable device such as a laptop, an electronic monitor, a projector, a television, and so on. The rendering of the norm can include other relevant information such as mental state data, mental state information, metrics, and so on. The rendering can compare norms for two or more types of media presentations. The media presentations can include advertisements and the advertisements can be represented by thumbnails. The flow 100 can further comprise comparing the metric for the advertisement to a norm for other advertisements 152. The rendering of the metrics for two or more advertisements can permit the determination of deviation from a norm or multiple norms for advertisements. The flow can further comprise modifying the media presentation 154 based on the metric that was generated. In some cases norms can be used to select one or more media presentations that best meet a set of predetermined goals for the presentations, based on metrics for the one or more presentations and how the metrics compare with norms. Media modifications can also be performed where, for example, if the metric for a proposed advertisement is found to be below a norm determined for similar advertisements, then the advertisement that deviates can be modified so that it more closely aligns with the norms for similar advertisements. However, if an advertisement is significantly better than a norm, then the advertisement can remain in its current state. Likewise, changes can be made to other media presentations based on deviations from the norms of other similar media presentations. The flow 100 can further comprise evaluating a personal analytic measure 156 for an individual where the personal analytic measure includes a norm for the individual. Personal analytic measures can be used to determine whether an individual is responding differently to a media presentation based on her or his own personal norm for similar media presentations. For example, if an individual's typical response to advertisements classified as humorous is a smile, and the individual does not smile when presented with a similarly classified "humorous" advertisement, a deviation in the individual response can be inferred for the advertisement. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors.

Figure 2:
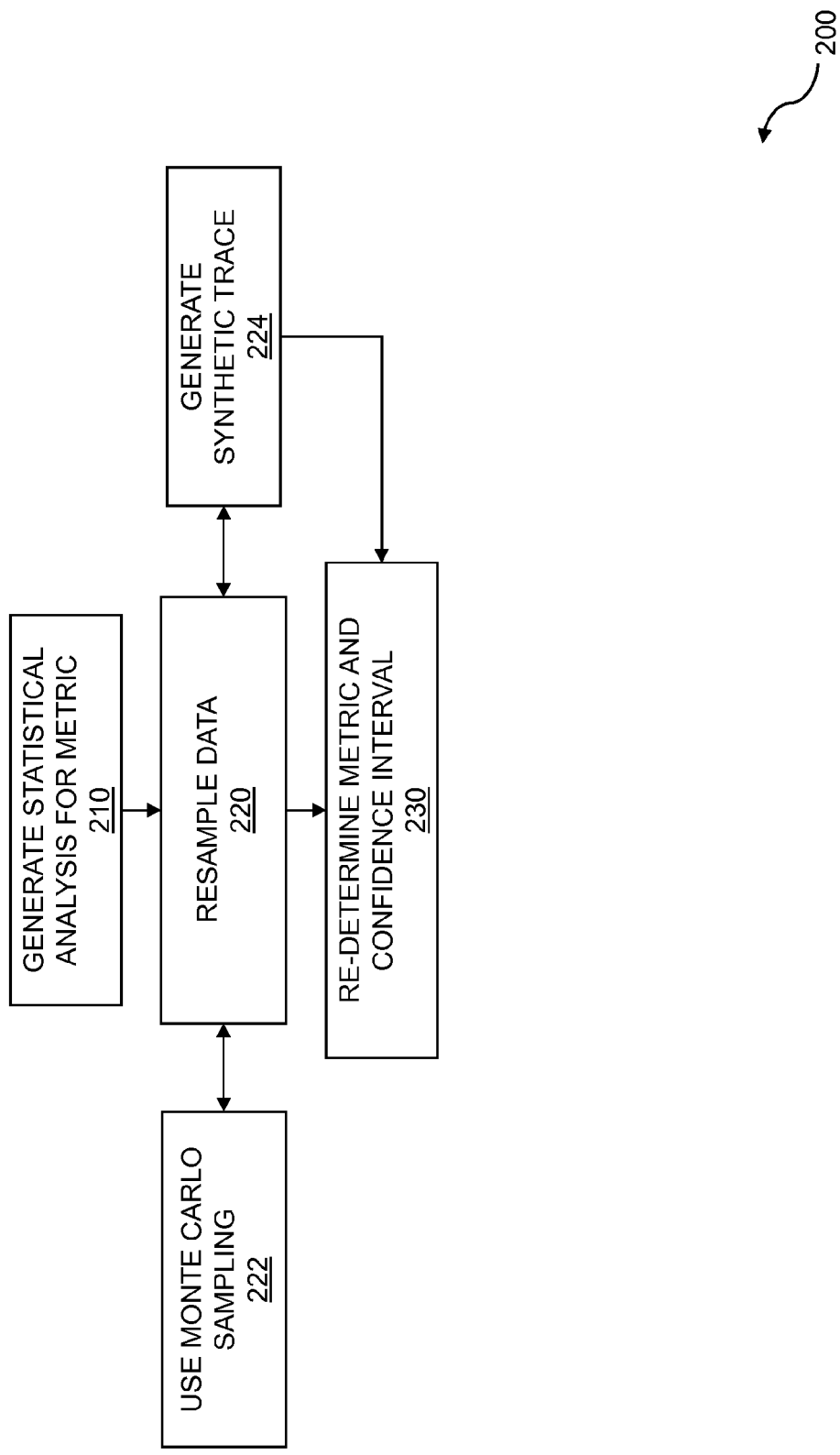
FIG. 2 is a flow diagram for resampling.

FIG. 2 is a flow diagram for resampling. The diagram 200 illustrates how resampling can aid the determining of norms for mental states. The flow 200 can continue from or be part of the previous flow 100, or the flow 200 can be performed independently of other flows in order to provide additional data analysis. The flow 200 includes generating statistical analysis for a metric 210. Mental state data is collected for one or more people. The data analyzed can be a time series. The mental state data can be analyzed in order to generate a metric associated with a mental state for one or more people. This metric can include a mean value and a variability value, or any other measure determined by performing statistical calculations on the mental state data. The metric can have confidence intervals pertaining to the value for the metric. To give an example of a metric, the case of a metric measuring the probability of a smile occurring can be examined. A mean smile value can be generated for a group of people as they experience a certain stimulus. A variance or standard deviance on the smile probability could then be calculated for the group of people.

The flow 200 also includes generating a statistical analysis for the metric by resampling data 220 from the mental state information by randomly sampling a certain number of times from the mental state data. The resampling can also be referred to as bootstrapping, and can comprise randomly and iteratively resampling data points with replacement in order to further clarify statistical trends and to further evaluate statistics related to the metric. That is, the data collected often represents a small portion of an overall population, so randomly resampling reveals statistical information that otherwise might have been missed. For example, if data has been collected on 60 individuals, bootstrapping or statistical resampling could involve randomly taking 60 samples from the pool of 60 original samples with replacement, allowing for any one individual to be sampled as few as 0 or as many as 60 times in this example bootstrapping pass while maintaining the integrity of the 60 data points (individuals). Iterating this sampling process 100 times, for example, statistically provides an accurate estimation of continually resampling the entire original pool of individuals, but accomplishes this while only using the 60 individuals who had been sampled previously. Thus the data collected on the one or more people is resampled 220 to aid in analysis. The resampling of the data can use a Monte Carlo sampling 222 routine or another type of selection technique. Once the data has been resampled, the resampling of the data can be used to generate a synthetic trace 224 to aid in producing the norm. Based on the resampling, a re-determined metric along with associated confidence intervals 230 can be found. In addition, the evaluating the norm can be based on resampling data from the mental state information from the plurality of people multiple times. This resampling can include random selection of data from the mental state information, typically be selecting data for a group of people within the plurality of people. Individuals from the plurality of people can be selectively omitted from the resampling. The omission can be based on demographic information, error indications in the data, or perceived outlier information. A synthetic trace can be generated based on the resampling where the synthetic trace indicates emotional reactions for grouped subsets of people within the plurality of people. The synthetic trace can be used to anonymize data and analysis thereof. The synthetic trace can be used in the generation and evaluating of the norm. The synthetic trace can be used to generate a norm once one or more outlier pieces of data are excluded. The synthetic trace can be used to generate multiple passes at a norm based on the resampling. The synthetic trace can indicate a trend that is produced based on the resampling of the subset of the samples. The trend information can aid in determining convergence of the norm based on the subset of the samples. The synthetic trace can be used to identify outlier pieces of data that can be eliminated. The synthetic trace can be used to produce the norm that can be used for the subset of the samples and for the larger set of samples. Synthetic traces can be generated using a variety of techniques including various statistical techniques. For example, the synthetic traces can be generated based on a uniform where the likelihood of a given individual in the subset of 60 individuals being selected is equal for each individual. The synthetic traces can be generated based on one or more weighting factors, where the weighting factors can include demographic data such as age, gender, race, national origin, and so on. The resampling can include stratified sampling where demographic variables are taking into account which describe a population of interest where individuals are then selected at random but still in proportion to demographic data on a test population. The resampling can include cluster sampling where demographic regions are divided into blocks, then perform random sampling is performed within those blocks. Various steps in the flow 200 may be changed in order, repeated, omitted, or the like without departing from the disclosed concepts. Various embodiments of the flow 200 may be included in a computer program product embodied in a non-transitory computer readable medium that includes code executable by one or more processors.

Figure 3:
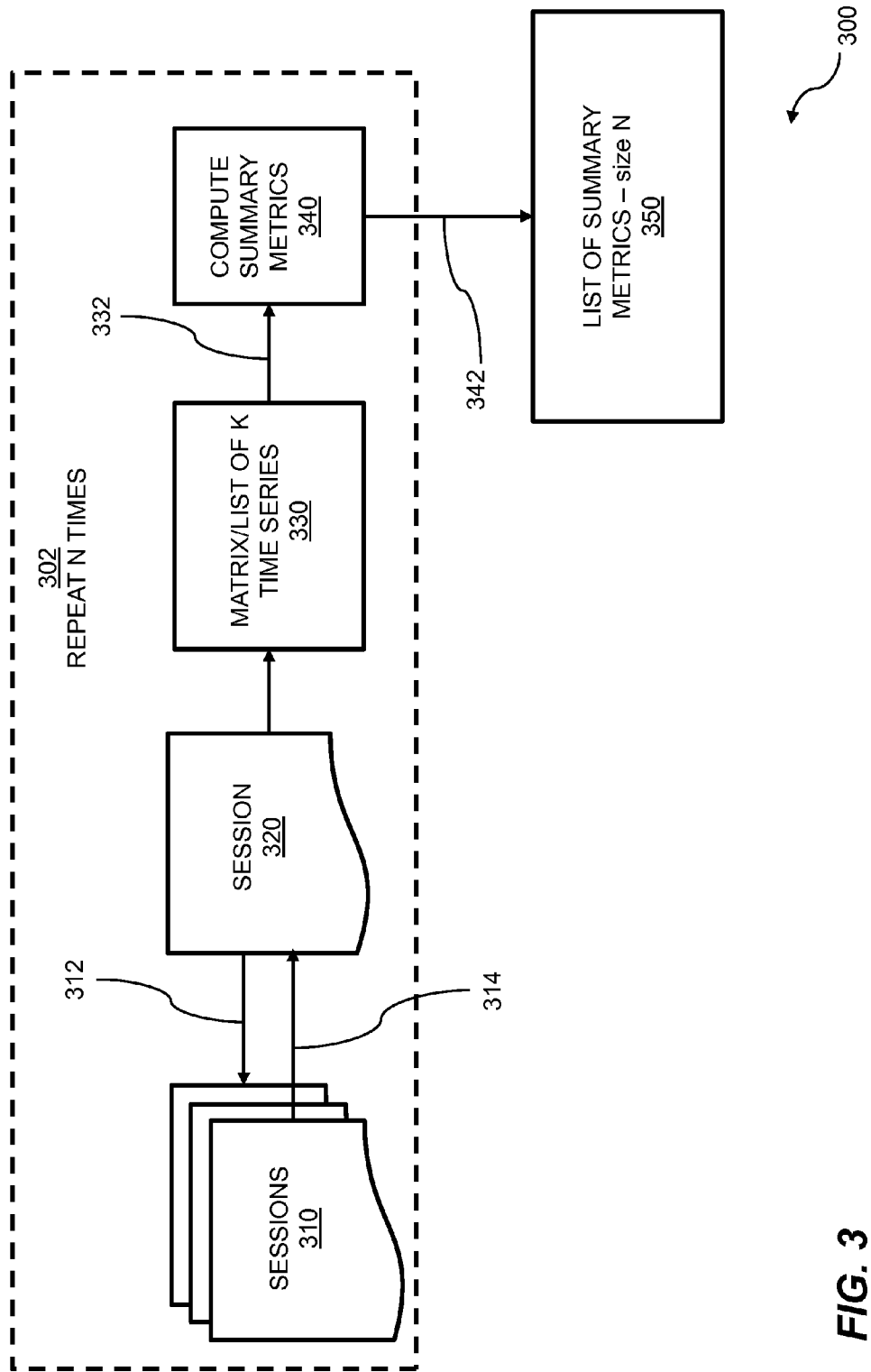
FIG. 3 is a flow diagram for sampling analysis.

FIG. 3 is a flow diagram for sampling analysis. The flow 300 shows how sampling analysis can aid in determining norms for mental states. The flow 300 can continue from or be part of the previous flow 100, the flow 200, or the flow 300, or can be performed independently of other flows to provide additional data analysis. Mental state data from a group of sessions 310 is collected. Each session can be considered to be data collected for an individual as they view media presentations. Information on the various individuals can also be used to delineate participant data, including a country of the person, a region for the person, a socioeconomic group for the person, a race of the person, an ethnicity of the person, a language group for the person, a market for the person, or a gender of the person. Other information that is obtained, in embodiments, includes product categories to which the media presentation relates. Information about the type or genre of the media presentation can also be used for evaluation, examples of genres including videos, movies, situation comedies, and so on. Further, an objective for the media presentation can be collected: solely among advertisements there are a multitude of possible objectives such as humor, educational objectives, drives to action, and so on. Relevant sessions can be determined for the statistical analysis. For instance, a certain demographic can be analyzed for a certain type of automobile advertisement while other demographics are not analyzed. From the relevant sessions, a session 320 is selected 312. Information on the session 320 is analyzed and information from the session is retained for statistical analysis. Sampling is accomplished by selecting 312 each of the relevant sessions, collecting data from the relevant sessions, and putting back 314 the sessions in the group of sessions 310. For this figure, it is assumed that "k" sessions are sampled. As a result, a matrix or list of "k" time series can be collected. The sampling process 302 can be repeated "n" times. In this manner, the list of "k" sessions can be sampled again "n" times, and thereby accomplish resampling. Statistical analysis 332 can be performed on the time series to compute summary metrics 340. The resulting summary metrics can include values for smiles, frustration, and other types of mental state analysis. The metrics can include means and variabilities for each of the mental states. A list of summary metrics 350 can be determined 342. In some embodiments, the determining can be performed by resampling data. Thus, metrics can be calculated based on statistics from a time series of the mental state information.

Figure 4:
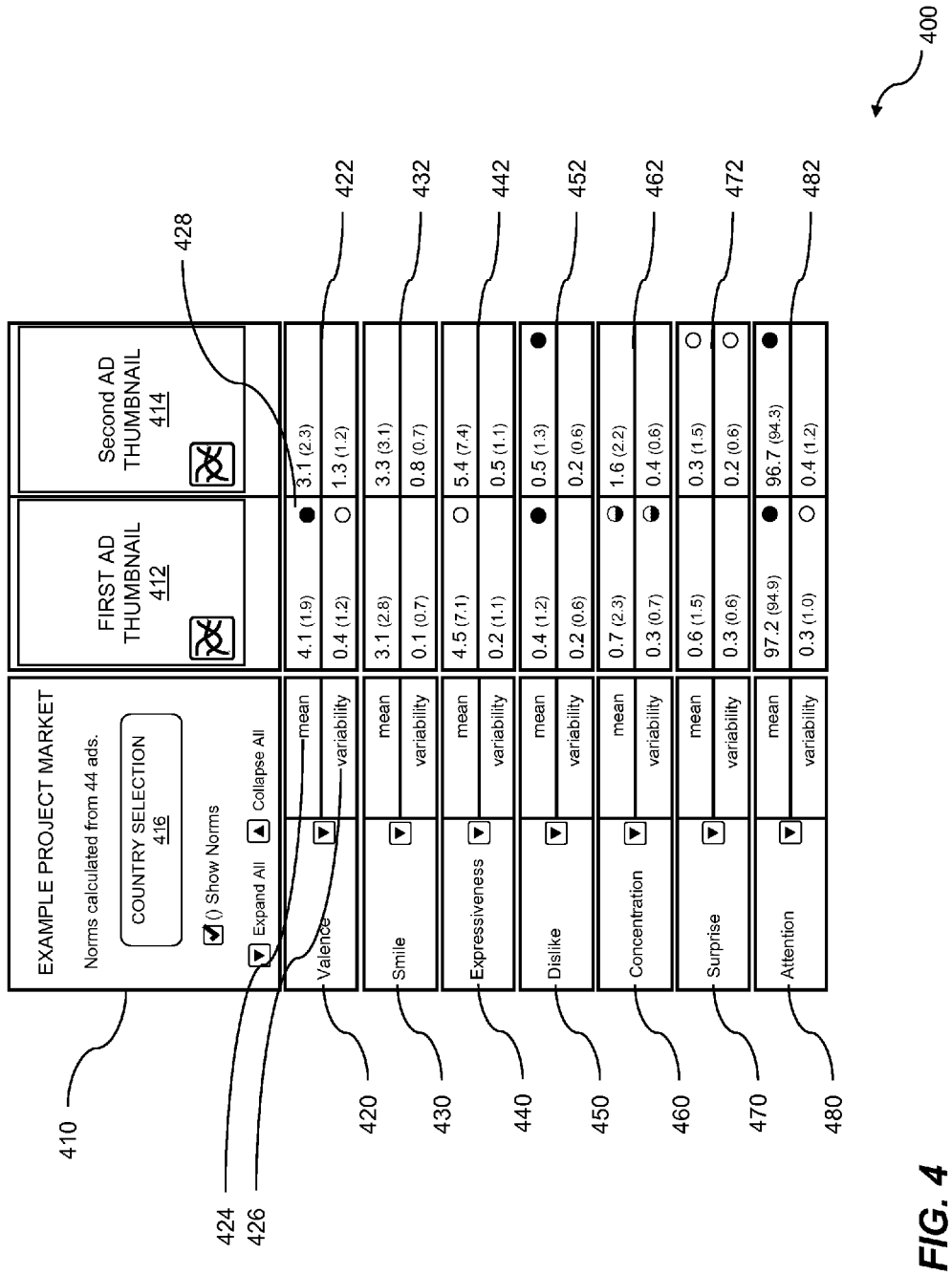
FIG. 4 shows an example rendering for norms.

FIG. 4 shows an example rendering for norms. Various rendering or graphical displays are possible to aid in the analysis of mental state. The renderings can compare metrics for various mental states with norms for those mental states. An example screen shot or tool display 400 is provided. A first ad thumbnail 412 is shown as well as a second ad thumbnail 414. Numerous thumbnails can be shown along with metrics and norms for the media presentations represented by the thumbnails. In some embodiments, the thumbnails are replaced by short video clips or other representations of the analyzed media presentations. A title section 410 is included and a button 416 is included for selecting between countries. In this case the norm box is checked and therefore norms are shown in the rendering as well as metrics. Other types of selections besides countries can be included such as region, socioeconomic group, race, ethnicity, language group, market, age, gender, emotional tone, media type, media duration, demographic, device, product category, and so on. In some cases, multiple selections can be made, or selections and sub-selections can be chosen. In the example given, mental states for valence 420, smile 430, expressiveness 440, dislike 450, concentration 460, surprise 470, and attention 480 are shown along with mean and variability values for each mental state. A mean and variability 422 can be provided for the valence 420. A mean and variability 432 can be provided for the smile score 430. A mean and variability 442 can be provided for the expressiveness score 440. A mean and variability 452 can be provided for the dislike score 450. A mean and variability 462 can be provided for the concentration score 460. A mean and variability 472 can be provided for the surprise score 470. A mean and variability 482 can be provided for the attention score 480.

In the example given, a mean 424 for valence is shown with values of 4.1 for advertisement 1 and 3.4 for advertisement 2. The norm for the valence mean is 1.9, as shown within the parenthesis. A variability 426 for valence is also shown with values of 0.4 and 1.3 for advertisement 1 and advertisement 2, respectively. The norm for the valence variance is 1.2, as shown within the parenthesis. When a metric value is significantly different from a norm value a demarcation can be included such as a colored or marked dot. A dot 428 can be a specific color (e.g. green) or be denoted with a specific shading or fill pattern and can denote a significantly higher valence than the norm. With a much higher valence indicating a much more positive than normal response, an advertisement can be expected perform at a higher level and therefore be much more effective. A significantly worse metric can be indicated by a dot of another color, such as red. For example, for an advertisement with a higher-than-typical mean and a lower-than-typical variance, the vast majority of responses will be clustered at the higher mean. Other observations can be denoted by other techniques such as bolding, dots of other colors, and the like. Analysis can be very narrow if desired. For example, a metric and norms can be provided for women in Japan responding to automotive advertisements shown on a mobile device, where the advertisements have a humorous emotional tone. A norm can therefore include a variance and the variance of reaction to a certain media presentation can be determined to be significantly different from a previous norm. Based on deviation from the norm the media presentation can be evaluated. In some cases, a higher change of emotion can indicate effectiveness of an advertisement, for instance.

Figure 5:
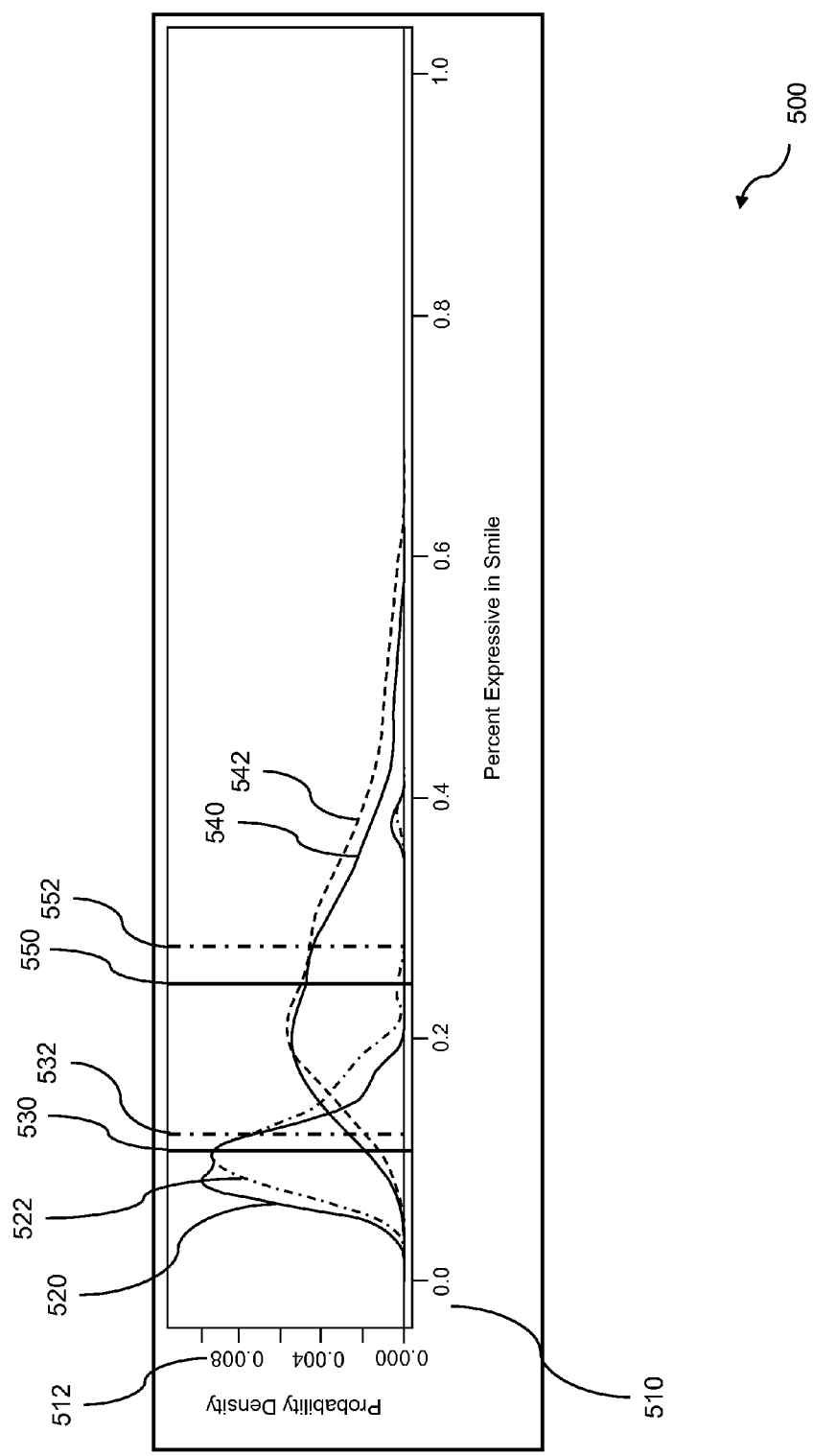
FIG. 5 is an example graph for smile tendency.

FIG. 5 is an example graph for smile tendency. Various graphs can aid in understanding mental states and normal mental state responses for different regions or demographics. The graph 500 shown illustrates example smile expressiveness for different regions. A smile can be used to understand enjoyment of an advertisement, for instance. In order to accurately interpret the data, in this case smile data, it is important to have an established norm value for the people observing the advertisement. The norm value can help identify typical results for a certain people, culture, gender, etc. In the diagram 500, the x-axis 510 shows a percentage of expressiveness for smiling. The y-axis 512 shows the probability density for the graph lines. Another line 520 shows expressiveness for smiling in response to a certain group of advertisements by individuals from a certain country, such as Indonesia, for example. Using the same smile classifier but with a different threshold for smiling, a line 522 is shown illustrating smile expressiveness in Indonesia in response to the advertisements. A mean 530 of 11% is shown for the first threshold while a mean 532 of 12% is shown for the second threshold. Another line 540 is shown for smile expressiveness by viewers in another country, such as the USA, for example, to the same group of advertisements. A mean 550 of 25% for the US viewers is shown as well. The line 542 is also shown for US viewers who are classified using the second threshold value for smiling. A corresponding mean 552 of 28% is shown as well. In this example, it can be seen that a much higher propensity to smile is seen in US viewers and this difference can be used to better analyze people's responses to media presentations. The ability to develop norms based on criteria such as nationality can aid in analysis, as knowledge of different norms within different cultures can prove critical to understanding mental state expression by residents of the countries. A norm can include a propensity to smile, a propensity to concentrate, a propensity to express, and so on.

Figure 6:
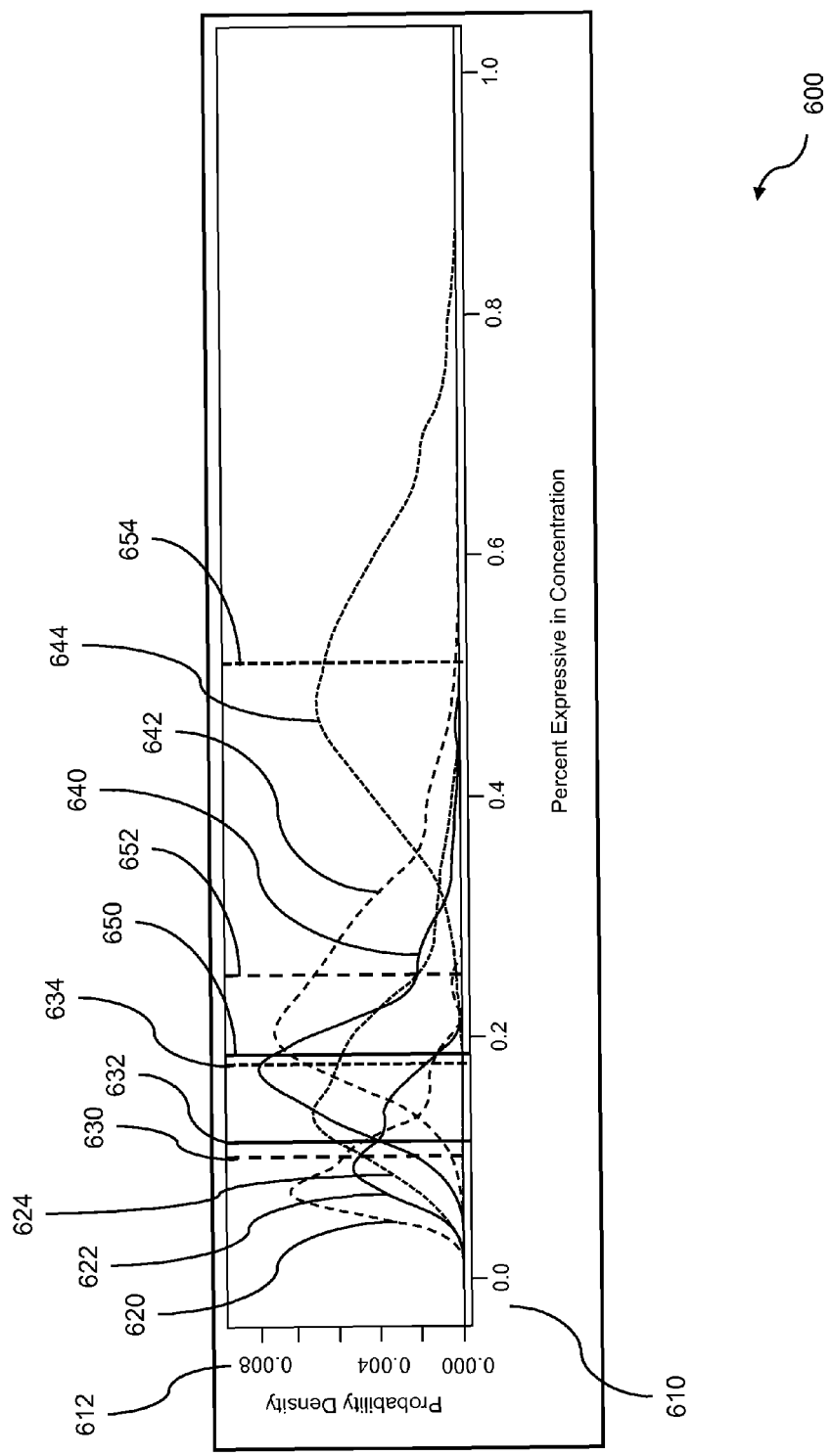
FIG. 6 is an example graph for tendency to concentrate.

FIG. 6 is an example graph for tendency to concentrate. A concentration graph can be useful in understanding how focused people are on a certain media presentation. For example, a lack of concentration can indicate that an advertisement is not engaging people. A normative value for a mental state such as concentration can be critical in understanding an individual's responses and how they compare with a norm. A graph 600 shows an example expressiveness value in the concentration of viewers from different countries. The x-axis 610 shows a percent expressiveness for concentrating. The y-axis 612 shows the probability density for the graph lines. In the example graph 600, the lines 620, 622, and 624 show concentration using different threshold values by viewers of advertisements in Indonesia. A 55% threshold line 620 is shown for concentration as well as a 50% threshold line 622 and a 10% threshold line 624. The corresponding mean values are shown using callouts 630, 632, and 634 respectively. In the example graph 600, threshold values are also given for US viewers, using lines 640, 642, and 644; the values have the same respective thresholds as the values given for the Indonesian viewers. Corresponding mean values 650, 652, and 654 are also shown. While a 10% threshold may only have a limited value, it is telling that even with this threshold number there is significant difference between Indonesian and US viewers. Understanding the different concentration expressiveness norms shown by different nationalities can aid in developing advertisements for different countries. Likewise, understanding norms for any other type of demographics can aid in market research analysis.

Figure 7:
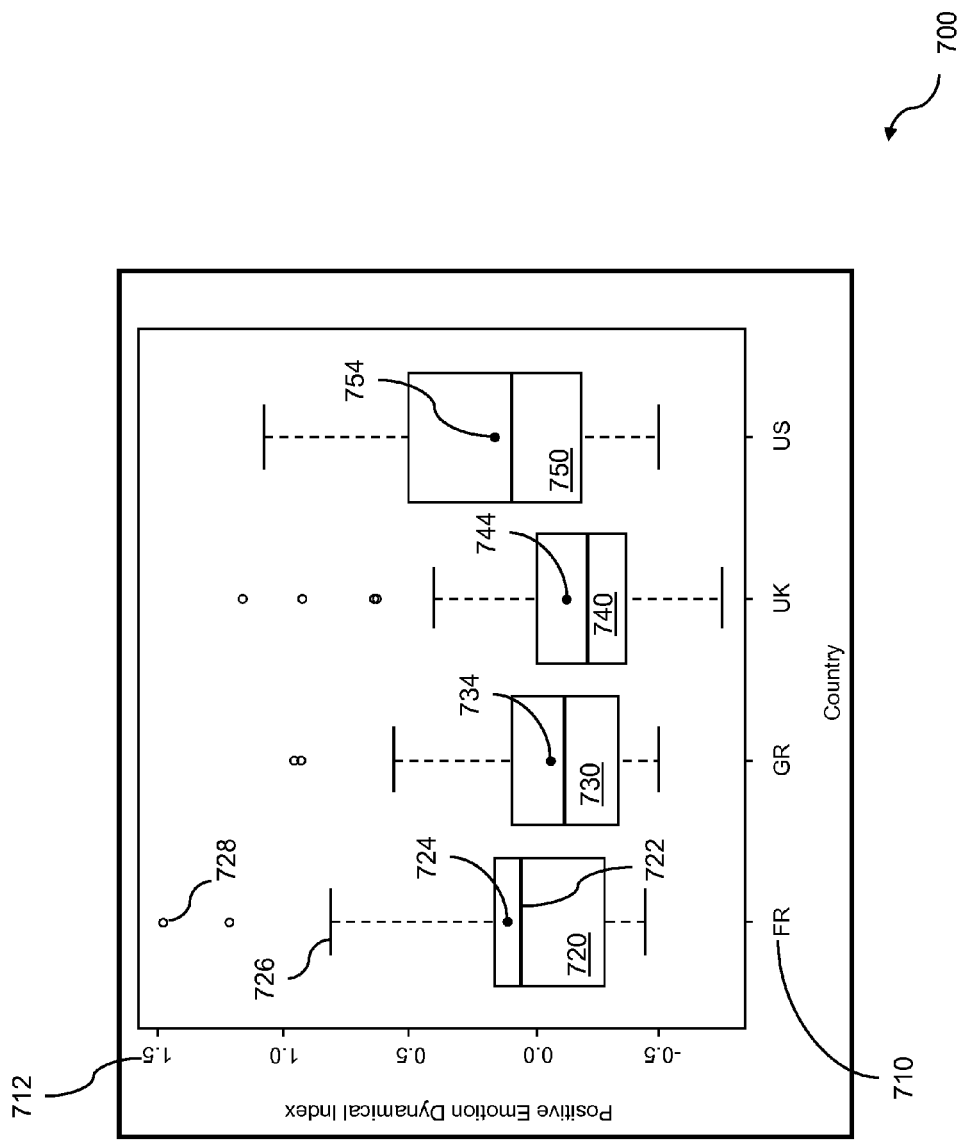
FIG. 7 shows example metrics and norms for countries.

FIG. 7 shows example metrics and norms for various countries. Metrics and norms can be used to understand and compare the mental states and reactions of people in different countries to given external stimuli. Recall that a metric can be used to apply a statistical value to mental state information and that a norm can be determined for one or more metrics. The example 700 shows metrics and norms for people in different countries 710 as they view media presentations. A metric for positive emotion dynamical index 712 is shown. This metric can be a combination of multiple pieces of mental state data including valence. In the example 700, the metrics for France, Greece, the United Kingdom, and the United States are shown along the x-axis. The graph 700 gives a box plot for each of these countries. A box 720 for France shows the range of values for viewers from France for the $25^{th}$ to $75^{th}$ percentile. Within the box 720 is a median line 722. A whisker line or confidence interval bar 726 is shown where observed points 728 outside the confidence interval are considered outliers. The average value 724 is shown using a dot. In this example, the average value 724 is considered a norm for viewers in France. Points outside the confidence interval, such as the point 728, can be flagged as being significantly different from the norm. A similar box plot with a variance norm could also be shown.

A box plot 730 for viewers in Greece is shown along with a norm 734. A box plot 740 for viewers in the United Kingdom is shown along with a norm 744. A box plot 750 for viewers in the United States is shown along with a norm 754. It should be noted that viewers in different countries have different mental state and emotional reactions and therefore that norms differ between countries. Understanding norms for the different countries can help understand the reactions of respondents from the countries. Understanding the norms can also aid in measuring the effectiveness of a given media presentation in each country.

Figure 8:
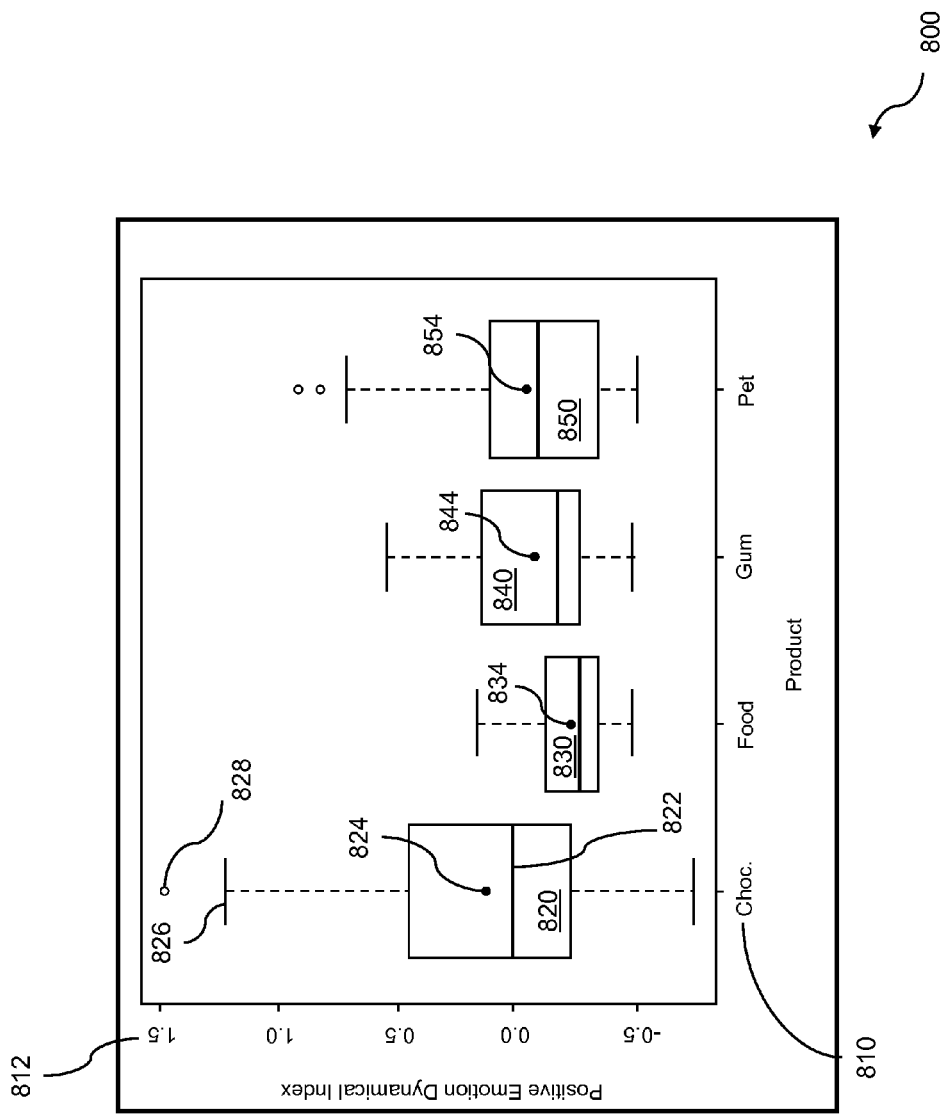
FIG. 8 shows example metrics and norms for products.

FIG. 8 shows example metrics and norms for advertisements on various products. Metrics and norms can be generated based on mental state data collected from people as they view or experience various media presentations, products, and so on. Understanding people's reactions to various presentations on certain products can be helpful in evaluating new products or advertisements for the products. The example graph 800 shows a box plot for mental state and emotional reactions to various products. A metric for positive emotion dynamical index 812 is shown. The metric can be a combination of multiple pieces of mental state data including valence. In the example 800, reactions to advertisements for chocolate, food, gum, and pets 810 are shown along the x-axis. A box 820 for chocolate shows the range of reactions, given here by numerical values, of people to a chocolate advertisement, with the values for the $25^{th}$ to $75^{th}$ percentile included. Within the box 820 is a median line 822. A whisker line or confidence interval bar 826 is shown where observed points 828 outside the confidence interval are considered outliers. The average value 824 is shown as a dot. In this example, the average value 824 is considered a norm for people viewing advertisements for chocolate. Points outside the confidence interval, such as the point 828, can be flagged as being significantly different from the norm. A similar box plot with a variance norm could also be shown.

In addition to the box plot 820 for people watching advertisements for chocolate, additional box plots are included in the graph 800. A box plot 830 for people watching an advertisement for food is shown along with a norm 834. A box plot 840 for people watching an advertisement for gum is shown along with a norm 844. A box plot 850 for people watching an advertisement for pets is shown along with a norm 854. It should be noted that viewers of different product advertisements have different mental state and emotional reactions and therefore that norms differ for those products. Understanding norms for the products can help understand respondents' reactions to the products.

Understanding the norms can also aid in measuring the effectiveness of a given advertisement for that type of product.

Figure 9:
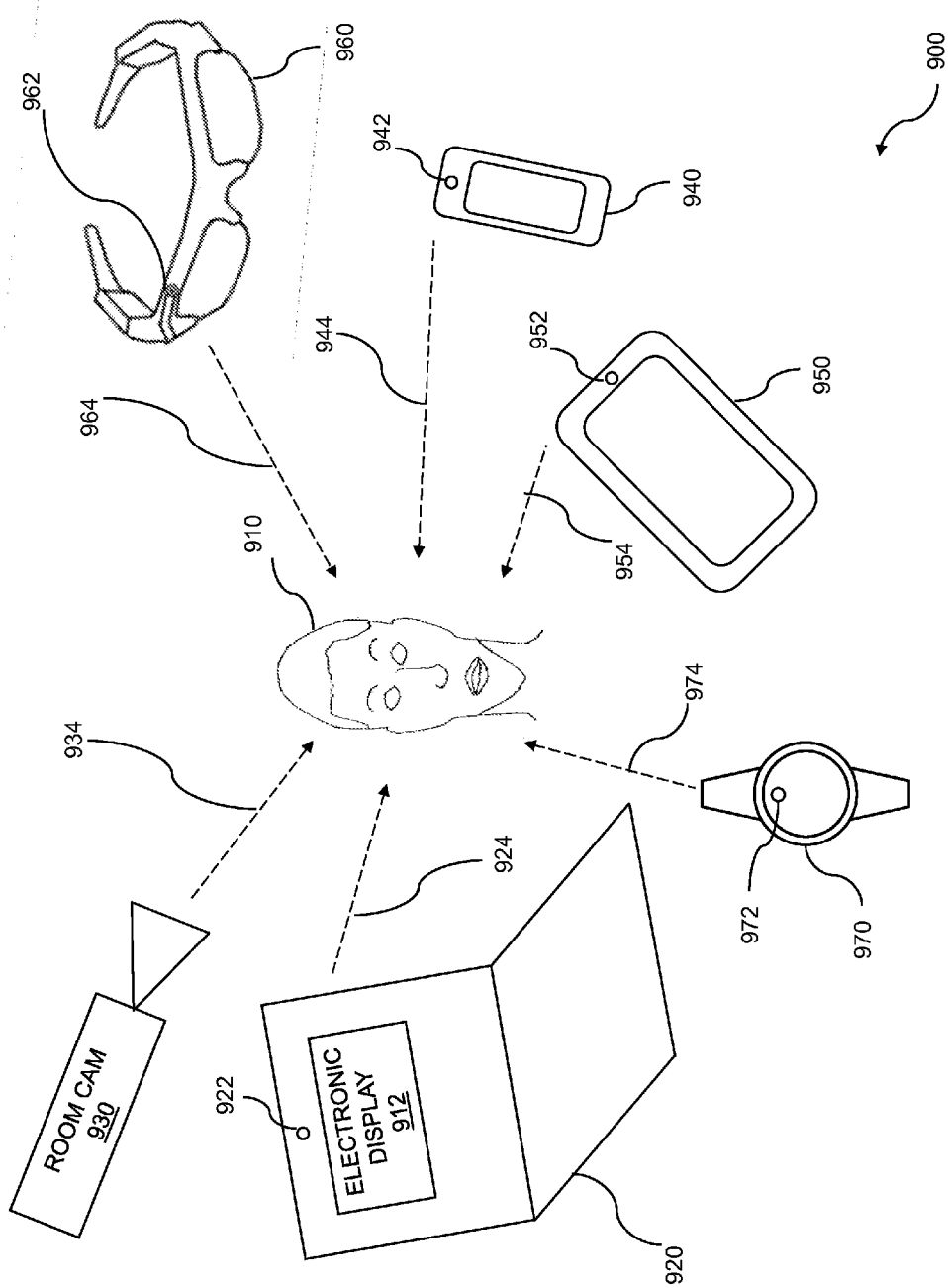
FIG. 9 shows example mental state data capture from multiple devices.

FIG. 9 shows example mental state data capture from multiple devices. Norms can be based on mental state data collected from multiple devices. Alternatively, norms can be developed on a device-by-device basis. In the latter situation, a norm can be individually determined for a tablet, a laptop, or another device. An engagement norm can be higher for a laptop, for instance, than for a tablet. The difference in value can be based on the understanding that since a laptop often is used for work while a tablet can be used for casual viewing, the propensity of an individual to concentrate is naturally higher when using a laptop. In another example, a frustration norm for a cell phone running an office productivity application can be deemed to be higher, due to the smaller screen and limited keyboard, than would be the case for the same or a similar application running on a full size laptop.

Mental state data can be obtained from multiple sources. At least one of the multiple sources can be a mobile device. Thus, facial data can be collected from a plurality of sources and used for mental state analysis. In some cases only one source is used for collection, while in other cases multiple sources can be used. A user 910 can be performing a task, viewing a media presentation on an electronic display 912, or doing any activity where it can be useful to determine the user's mental state. The electronic display 912 can be on a laptop computer 920 as shown, a tablet computer 950, a cell phone 940, a desktop computer monitor, a television, or any other type of electronic device. The mental state data can be collected on a mobile device such as a cell phone 940, a tablet computer 950, or a laptop computer 920; a fixed device, such as a room camera 930; or a wearable device such as glasses 960 or a watch 990. The plurality of sources can include at least one mobile device such as a phone 940 or a tablet 950, or a wearable device such as glasses 960 or a watch 970. A mobile device can include a forward facing camera and/or rear facing camera which can be used to collect video and/or image data.

As the user 910 is monitored, the user 910 can move due to the nature of the task, boredom, distractions, or for another reason. As the user moves, the user's face can be visible from one or more of the multiple sources. For example, if the user 910 is looking in a first direction, the line of sight 924 from the webcam 922 might be able to observe the individual's face, but if the user is looking in a second direction, the line of sight 934 from the room camera 930 might be able to observe the individual's face. Further, if the user is looking in a third direction, the line of sight 944 from the phone camera 942 might be able to observe the individual's face. If the user is looking in a fourth direction, the line of sight 954 from the tablet cam 952 might be able to observe the individual's face. If the user is looking in a fifth direction, the line of sight 964 from the wearable camera 962 might be able to observe the individual's face. If the user is looking in a sixth direction, the line of sight 974 from the wearable camera 972 might be able to observe the individual's face. Another user or an observer can wear the wearable device, such as the glasses 960 or the watch 970. In other embodiments, the wearable device is a device other than glasses, such as an earpiece with a camera, a helmet or hat with a camera, a clip-on camera attached to clothing, or any other type of wearable device with a camera or another sensor for collecting mental state data. The individual 910 can also wear a wearable device including a camera which can be used for gathering contextual information and/or collecting mental state data on other users. Because the individual 910 can move their head, the facial data can be collected intermittently when the individual is looking in the direction of a camera. In some cases, multiple people are included in the view from one or more cameras, and some embodiments include filtering out faces of one or more other people to determine whether the individual 910 is looking toward a camera. A norm can thus be determined using mental state data from a collection of devices. Likewise, mental state data can be analyzed separately for the various devices and a norm developed for one or more of the devices.

Figure 10:
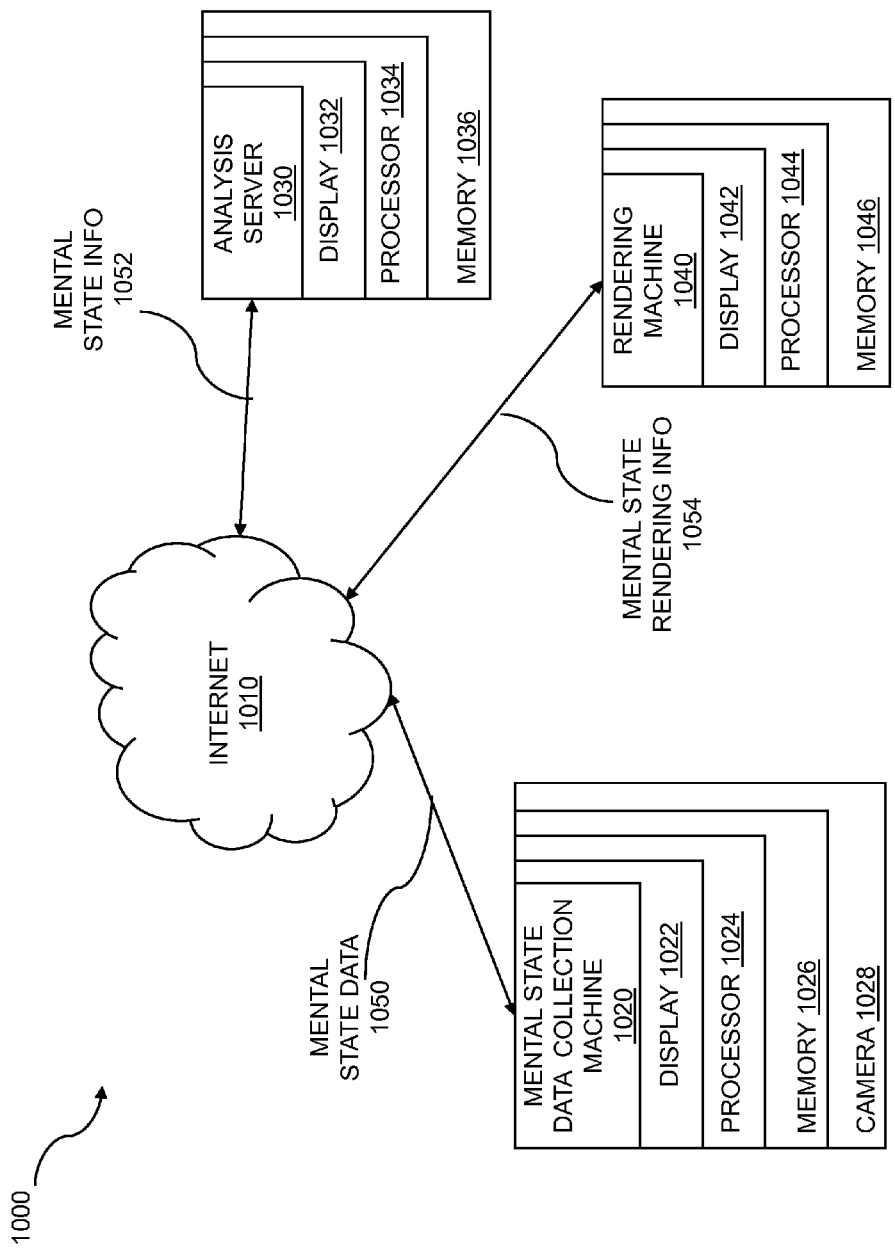
FIG. 10 is a system diagram for norms and mental state analysis.

FIG. 10 is a system diagram for norms and mental state analysis. The diagram illustrates an example system 1000 for mental state collection, analysis, and rendering. This system 1000 can be used for norm generation and usage. The system 1000 can include one or more client machines or mental state data collection machines or devices 1020 linked to an analysis server 1030 via the Internet 1010 or another computer network. Mental state data 1050 can be sent from the mental state data collection machines 1020 to other computing devices via the Internet 1010 or other network. The client machine 1020 comprises one or more processors 1024 coupled to a memory 1026 which can store and retrieve instructions, a display 1022, and a camera 1028. The memory 1026 can be used for storing instructions, mental state data, mental state information, mental state analysis, norms, and market research information. The display 1022 can be any electronic display, including but not limited to, a computer display, a laptop screen, a net-book screen, a tablet computer screen, a cell phone display, a mobile device display, a remote with a display, a television, a projector, or the like. The camera 1028 can comprise a video camera, still camera, thermal imager, CCD device, phone camera, three-dimensional camera, depth camera, multiple webcams used to show different views of a person, or any other type of image capture apparatus that can allow captured data to be used in an electronic system. The processors 1024 of the machine 1020 can be configured to receive mental state data from people, and in some cases to analyze the mental state data to produce mental state information. The mental state information can be output in real time (or near real time), based on mental state data captured using the camera 1028. In other embodiments, the processors 1024 of the client machine 1020 are configured to receive mental state data from one or more people, analyze the mental state data to produce mental state information, and send the mental state information 1052 to the analysis server 1030.

The analysis server 1030 can comprise one or more processors 1034 coupled to a memory 1036 which can store and retrieve instructions, and a display 1032. The analysis server 1030 can receive mental state data and analyze the mental state data to produce mental state information so that the analyzing of the mental state data can be performed by a web service. The analysis server 1030 can use mental state data or mental state information received from the client machine 1020. The received data and other data and information related to mental states and analysis of the mental state data can be considered mental state analysis information 1052 and can be transmitted to and from the analysis server using the internet or another type of network. In some embodiments, the analysis server 1030 receives mental state data and/or mental state information from a plurality of client machines and aggregates the mental state information. The analysis server can evaluate metrics and calculate norms for mental states.

In some embodiments, a displayed rendering of mental state analysis can occur on a different computer than the device 1020 or the analysis server 1030. This computer can be termed a rendering machine 1040, and can receive mental state rendering information 1054, mental state analysis information, mental state information, norms, deviations from norms, and graphical display information collectively referred to as mental state rendering information 1054. In embodiments, the rendering machine 1040 comprises one or more processors 1044 coupled to a memory 1046 which can store and retrieve instructions and a display 1042. The rendering can be any visual, auditory, or other form of communication to one or more individuals. The rendering can include an email, a text message, a tone, an electrical pulse, or the like.

The system 1000 can include computer program product embodied in a non-transitory computer readable medium for mental state analysis comprising: code for obtaining mental state data from a plurality of people; code for analyzing the mental state data to produce mental state information for the plurality of people; code for generating a metric based on the mental state information; and code for evaluating a norm based on the metric. The system 1000 can perform a computer-implemented method for physiology analysis comprising: receiving mental state data from a plurality of people; analyzing the mental state data to produce mental state information for the plurality of people; generating a metric based on the mental state information; and evaluating a norm based on the metric. The system 1000 can perform a computer-implemented method for mental state analysis comprising: receiving mental state information based on analysis of mental state data obtained mental state data from a plurality of people along with a metric based on the mental state information and a norm based on the metric; and rendering an output of the norm.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for mental state analysis comprising:
   obtaining mental state data from a plurality of people by capturing images of the plurality of people and analyzing the images to determine the mental state data, wherein, for at least one person of the plurality of people, the capturing is performed while the at least one person views a media presentation;
   analyzing the mental state data to produce mental state information for the plurality of people;
   generating a metric based on the mental state information;
   generating a statistical analysis for the metric by resampling data from the mental state information by randomly sampling a specific number of times from the mental state information;
   modifying the media presentation based on the metric;
   evaluating a norm, on a computing device, based on the metric, wherein the evaluating the norm is based on resampling data from the mental state information from the plurality of people multiple times where the resampling includes random selection of data from the mental state information and where individuals from the plurality of people are selectively omitted from the resampling and where a synthetic trace is generated based on the resampling and the synthetic trace indicates emotional reactions for grouped subsets of people within the plurality of people and the synthetic trace is used in the evaluating of the norm; and
   rendering an output of the norm on a display.

2. The method of claim 1 wherein the norm is determined for a certain demographic.

3. The method of claim 2 wherein the norm is determined for a country, a region, a socioeconomic group, a race, an ethnicity, a language group, a market, an age group, or a gender.

4. The method of claim 1 wherein the norm is determined for a product category, a media length, a media type, or a gaze direction.

5. The method of claim 1 wherein the norm includes a variance and where the variance of reaction to a certain media presentation is determined to be significantly different from a previous norm.

6. The method of claim 1 wherein the norm includes a mean value and a standard deviation value indicative of a mental state and variability on the mental state where the norm indicates a collective response by the plurality of people to a media presentation.

7. The method of claim 1 wherein the norm includes a propensity to smile, a propensity to concentrate, or a propensity to express.

8. The method of claim 1 wherein the norm is determined on a basis for a device.

9. The method of claim 1 wherein the norm represents an emotion norm for a group.

10. The method of claim 1 wherein the mental state data from the plurality of people is collected while the plurality of people are exposed to a media presentation.

11. The method of claim 10 wherein the norm is determined in response to a category of media presentations.

12. The method of claim 10 wherein the media presentation includes an advertisement.

13. The method of claim 12 further comprising comparing the metric for the advertisement to the norm for other advertisements.

14. The method of claim 1 further comprising evaluating a personal analytic measure for an individual where the personal analytic measure includes a norm for the individual.

15. The method of claim 1 wherein the mental state data includes facial data and the metric and the norm are a reflection of the facial data.

16. The method of claim 1 further comprising collecting additional mental state data and comparing the additional mental state data against the norm.

17. The method of claim 16 further comprising identifying a deviation by the additional mental state data from the norm.

18. The method of claim 1 wherein the metric is calculated based on statistics from a time series of the mental state information.

19. The method of claim 1 wherein the norm is calculated across a number of media presentations.

20. The method of claim 1 wherein the resampling of the data is used to generate a synthetic trace used in generating the norm.

21. The method of claim 1 further comprising inferring mental states based on the mental state data which was obtained wherein the mental states include one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, and curiosity.

22. The method of claim 1 further comprising determining context during which the mental state data is captured.

23. A computer program product embodied in a non-transitory computer readable medium for mental state analysis, the computer program product comprising code which causes one or more processors to perform operations of:
   obtaining mental state data from a plurality of people by capturing images of the plurality of people and analyzing the images to determine the mental state data, wherein, for at least one person of the plurality of people, the capturing is performed while the at least one person views a media presentation;

analyzing the mental state data to produce mental state information for the plurality of people;
generating a metric based on the mental state information;
generating a statistical analysis for the metric by resampling data from the mental state information by randomly sampling a specific number of times from the mental state information;
modifying the media presentation based on the metric;
evaluating a norm, on a computing device, based on the metric, wherein the evaluating the norm is based on resampling data from the mental state information from the plurality of people multiple times where the resampling includes random selection of data from the mental state information and where individuals from the plurality of people are selectively omitted from the resampling and where a synthetic trace is generated based on the resampling and the synthetic trace indicates emotional reactions for grouped subsets of people within the plurality of people and the synthetic trace is used in the evaluating of the norm; and
rendering an output of the norm on a display.

24. A computer system for mental state analysis comprising:
a memory which stores instructions;
one or more processors attached to the memory wherein the one or more processors, when executing the instructions which are stored, are configured to:
obtain mental state data from a plurality of people by capturing images of the plurality of people and analyzing the images to determine the mental state data, wherein, for at least one person of the plurality of people, the capturing is performed while the at least one person views a media presentation;
analyze the mental state data to produce mental state information for the plurality of people;
generate a metric based on the mental state information;
generate a statistical analysis for the metric by resampling data from the mental state information by randomly sampling a specific number of times from the mental state information;
modify the media presentation based on the metric;
evaluate a norm, on a computing device, based on the metric, wherein the evaluating the norm is based on resampling data from the mental state information from the plurality of people multiple times where the resampling includes random selection of data from the mental state information and where individuals from the plurality of people are selectively omitted from the resampling and where a synthetic trace is generated based on the resampling and the synthetic trace indicates emotional reactions for grouped subsets of people within the plurality of people and the synthetic trace is used in the evaluating of the norm; and
render an output of the norm on a display.

25. A computer-implemented method for mental state analysis comprising:
obtaining mental state data from a plurality of people by capturing images of the plurality of people and analyzing, using one or more processors, the images to determine the mental state data, wherein, for at least one person of the plurality of people, the capturing is performed while the at least one person views a media presentation;
analyzing the mental state data to produce mental state information for the plurality of people;
generating a metric based on the mental state information;
generating a statistical analysis for the metric by resampling data from the mental state information by randomly sampling a specific number of times from the mental state information;
evaluating a norm, on a computing device, based on the metric, wherein the evaluating the norm is based on resampling data from the mental state information from the plurality of people multiple times where the resampling includes random selection of data from the mental state information and where individuals from the plurality of people are selectively omitted from the resampling and where a synthetic trace is generated based on the resampling and the synthetic trace indicates emotional reactions for grouped subsets of people within the plurality of people and the synthetic trace is used in the evaluating of the norm;
modifying the media presentation based on the metric; and
displaying the modified media presentation.

* * * * *